US006987026B1

(12) United States Patent
Choi et al.

(10) Patent No.: US 6,987,026 B1
(45) Date of Patent: Jan. 17, 2006

(54) **VECTOR FOR THE TRANSFORMATION OF *PHAFFIA RHODOZYMA* AND PROCESS OF TRANSFORMATION THEREBY**

(75) Inventors: Eui-Sung Choi, Taejon-si (KR); Sang-Ki Rhee, Seoul (KR); Jung-Hoon Sohn, Taejon-si (KR); Soo-Dong Park, Taejon-si (KR); Yoon Hyoung Lee, Kyoungki-do (KR); Seung Jae Lee, Kyoungki-do (KR); Jae Kweon Jang, Seoul (KR); Seok Keun Choi, Seoul (KR); Young Rok Son, Seoul (KR)

(73) Assignees: Korea Institute of Science and Technology, Seoul (KR); Haitai Confectionery Co., Ltd., Seoul (KR)

( * ) Notice: Subject to any disclaimer, the term of this patent is extended or adjusted under 35 U.S.C. 154(b) by 0 days.

(21) Appl. No.: 09/830,691

(22) PCT Filed: May 29, 1999

(86) PCT No.: PCT/KR99/00265

§ 371 (c)(1),
(2), (4) Date: Apr. 26, 2001

(87) PCT Pub. No.: WO00/26387

PCT Pub. Date: May 11, 2000

(30) Foreign Application Priority Data

Oct. 31, 1998 (KR) ............................... 1998 46547

(51) Int. Cl.
*C12N 1/19* (2006.01)
*C12N 15/63* (2006.01)
*C12N 15/64* (2006.01)
*C12N 15/81* (2006.01)
*C07H 21/04* (2006.01)

(52) U.S. Cl. ...................... 435/483; 435/471; 435/476; 435/320.1; 435/254.11; 435/455; 435/461; 536/23.1; 536/23.2; 536/23.7

(58) Field of Classification Search ............. 435/320.1, 435/483, 455, 461; 536/23.1, 23.7, 24.1, 536/23.2
See application file for complete search history.

(56) References Cited

FOREIGN PATENT DOCUMENTS

WO    WO 94/06918    3/1994
WO    WO 97/23633    3/1997

OTHER PUBLICATIONS

I.G. Kim et al., Mar. 31, 1999, GenBank Accession No. AF004672.
I.G. Kim et al., Mar. 18, 1999, GenBank Accession No. AF016256.
E. Mutoh et al., "Inducible Expression of a Gene Encoding an L41 Ribosomal Protein Responsible for the Cycloheximide-Resistant Phenotype in the Yeast *Candido maltosa*," Journal of Bacteriology, 1995, 177(18):5383-5386.
K. Kondo et al., "A Transformation System for the Yeast *Candido utilis* Use of a Modified Endogenous Ribosomal Protein Gene as a Drug-Resistant Marker and Ribosomal DNA as an Integration Target for Vector DNA," Journal of Bacteriology, 1995, 177(24):7171-7177.
P. Dehoux et al., "Natural cycloheximide resistance in yeast The role of ribosomal protein L41," Eur. J. Biochem, 1993, 213:841-848.
L. Del Pozo et al., "Two different genes from *Schwanniomyces occidentalis* determine ribosomal resistance to cycloheximide," Eur. J. Biochem, 1993, 213:849-857.
CH. T. Roberts et al., "A Cycloheximide-resistant Mutant of *Tetrahymena Pyriformis*," Experimental Cell Research, 1973 81:312-316.
I.-G. Kim et al., "Cloning of the Ribosomal Protein L41 Gene of *Phaffia rhodozyma* and Its Use as a Drug Resistance Marker for Transformation," Applied and Environmental Microbiology, 1998, 64(5):1947-1949.
J. Wery et al., "High copy number integration into the ribosomal DNA of the yeast *Phaffia rhodozyma*," Gene, 1997, 184:89-97.
S. Kawai et al., "Drastic Alteration of Cycloheximide Sensitivity by Substitution of One Amino Acid in the L41 Ribosomal Protein of Yeasts," Journal of Bateriology, 1992, 174(1):254-262.

*Primary Examiner*—David Guzo
(74) *Attorney, Agent, or Firm*—Gates & Cooper LLP

(57) ABSTRACT

The present invention is directed to a recombinant vector for transforming yeast and a process for transforming yeast thereby, more particularly to a recombinant vector comprising a gene encoding a mutated L41 protein having cycloheximide-resistant activity and a ribosomal DNA. The recombinant vector and the process for transforming thereby of the present invention is applicable to the efficient and stable integration of desired foreign DNA into yeast genome, thus providing useful tools for the production of a natural pigment, astaxanthin.

6 Claims, 5 Drawing Sheets

FIG. 1

```
 -704 AAGAGCTATTTGAATGACGACCACAAGAGTGACGATCATATTGAGCATAGTATACCAAAGGCCAAGAGGC
 -634 TGTGTGGTGTTCTATGAGTGGCCTTGATTATGTGTTACATAAATAAACTGATCT[CAAT]TTTCAAATACT
 -564 TGCCAACACTTTCA[TATA]TCACACCAAAAAAAGTCAGATTGGCCCACAAAGTCAGATACACGCTCGATC
 -494 GTCGACGGGTTCAAGCACTTTGTCAGGCGAAAGAAAGGCCACAGCACCACCCTTCAAGTCTCGTCTCAAT
 -424 CAGGTTCGTCTAGCTTTTTGTGTGCAAGGATTTACCGTCTTGATGGATTTGTTCGTTGAAAGAGAGGAAA
 -354 GAACATGCTGAACTGACGAAAGTGTGAACAAAAATTGTGATTTTTTCATTGTGTTTCGCTGGTCTCCTT
 -284 GCTGGGTTGGGTTGGATCGGATTTATCTTCTGTGTTGGATGGAAAACCCTGAATGTTCTTTTCTTGGACA
 -214 TCTTCTAAACTCGACAAAACGATTCATTCCTCCGTACTGCTCTGGTTCTGCCTTTTTGAATCGCATCGAT
 -144 AAATTCTTCCCTCGGAACGTTCGATCAATCTCCGTCAAACTTATCATCCAAAAATCTCTTCTCGACTGCC
  -74 GCCTTGCTCCTTTTCTTCGTTCTTTCCTTAATCCGCTTTCGACTACCCTCCTTCTCTTCACACTCATAGT
   -4 CAAG ATG GTC AAC GTT CCC AAG ACT CGA CGTGAGTTATAGCAATTTCAACAACTCTCCAGA
         M   V   N   V   P   K   T   R   R
   53 CGACAAATATTCCAGTGCATCGAAAGAGTTTGTGGATAAACGCGACAGTTTCAAGGGAAAGAGTCGATGG
  123 ACAGATTTGGAAGACTTAGCCGGTCAAGGAACTTGGGGATCACGTGGCGGAGGACTCATCAGAAGAAGTC
  193 GGGATTTGTTTGATCATAGTGGGATCAAGACAAACTGGAGGATATGGCTCGCCTTGGAAGGGAATCTCCG
  263 GCCTGGATTCGAGGATCCGAAAGTTGTACGTATGGAAAAGCTTACACGGCTTGGATTTATTATCTTTCAT
  333 AGGA ACC TAC TGC AAG GGT AAG GCT TGC AAG AAG CAC ACGTAAGTCGCTTATCCTCTC
        T   Y   C   K   G   K   A   C   K   K   H   T
  391 CACTCTTTCATGGCATATTGTCAACGACTGGACAACGCGTCCGTTTTGAAACAAGTGACTTACCTGTGAA
  461 ATTTGATTCTACACCTGTATTTAGC CCT CAC AAG GTACATATCACATCCTCCCACCCCACCCTGCC
                              P   H   K
  527 CAACTTCTTCAGTTCATCTTGCTCTCGGTTTCCACATTCCCTGATGACCTCCTTGTATGTTCTTTGCGAA
  597 CGTTTGTTTCTGTTTCTGTAGGTG ACC CAG TAC AAG AAG GGA AAG GAC TCC ATC TTC G
                              V   T   Q   Y   K   K   G   K   D   S   I   F   A
  655 CC CAG GGA AAG CGA CGA TAC GAC CGA AAG CAG TCC GGT TAC GGA GGT CAG ACC
        Q   G   K   R   R   Y   D   R   K   Q   S   G   Y   G   G   Q   T
  708 AAG CCC GTT TTT CAC AAG AAG GCT AAG ACC ACC AAG AAG GTC GTC CTT CGA TT
      K  (P)  V   F   H   K   K   A   K   T   T   K   K   V   V   L   R   L
  761 G GGTACGTTTTGTTTATTTTGAATTCTTTTTGTGTATGCAGACTTTTGATGATTATGCTCCTCTGTCG
      E
  830 TTTTTTCTCTTCAAACAGAG TGC TCC GTC TGC AGTTCGTTCTTCCTTCCAACCAAAACTTCAACT
                          C   S   V   C
  895 ACAGACATCATAAACAGACATCTTACTTCGGTGTTCTCTCTTTTTTTCCGCAGAG TAC AAG ATG CA
                                                              Y   K   M   Q
  961 G ATG ACC CTC AAG CGA TGC AAG CAC TTC GAG CTT GGA GGA GAC AAG AAG ACC
        M   T   L   K   R   C   K   H   F   E   L   G   G   D   K   K   T
 1013 AAG GGTTCGTCTTTTGTCCATATATTCTCTGGTTCACTTCTTATGTTCCTAACGTACTTGTTTCCTTTT
      K   G
 1082 TGGTTCGGATGTTGTTTCTATCGGTGGTGTTTTCTTTTCTTTGGATGCATTATCATTTATCGTGTTGGAC
 1152 TGTTTTCCTCTGCTCGTTTCTTTCTCCTCTGTACTTGTGCTTCTCAGGA GCC GCC ATC TCT TTC
                                                       A   A   I   S   F
 1216 TAA ATGGTTGTTTTAACCCCGTCGTCTCCACCATATGTCAAATCGGCATGCGCGTTGTCCCTTCCAATC
      *
 1285 AGTCGTTTCCATGCTCGAGATACTTCTTGGACGTTCTTGGGGAGCAATTACACATCGAGAAAATACCCA
 1355 AAAAACCACGCACCCCCTTTTATTTCAATGGGGAGATCTGGATCTATGTATCATGTCGATTTTCTATTTC
 1425 CCAAAACCCATTGATTGTTCATCTCCTCTTAAGAGTAACATCTTTTCCAAGATACTTCTC
```

VECTOR FOR THE TRANSFORMATION OF PHAFFIA RHODOZYMA AND PROCESS OF TRANSFORMATION THEREBY

FIELD OF THE INVENTION

The present invention is directed to a novel vector for transforming yeast and to a process for transforming yeast thereby. Particularly, the present invention is directed to a gene encoding L41, a ribosomal protein derived from *Phaffia rhodozyma* which is useful for producing natural pigment astaxanthin; a gene encoding a mutated L41 protein having a cycloheximide-resistant activity; a ribosomal DNA derived from *Phaffia rhodozyma*; a vector for transforming *Phaffia rhodozyma* stably, comprising said gene encoding a mutated L41 protein and said ribosomal DNA; and a process for transforming *Phaffia rhodozyma* thereby.

BACKGROUND

*Phaffia rhodozyma* is a reddish yeast species producing astaxanthin, a useful natural pigment. Astaxanthin is a member of the carotenoids, which are represented by β-carotene, a precursor of vitamin A. Astaxanthin as a main pigment of curstacea, trout and salmon is widely distributed in nature. However, they cannot synthesize astaxanthin and should be supplied with it from a diet. Thus, it has been considered necessary to add the pigment in the cultivation of crustacea, trout and salmon, because the added pigments to the crustacea and fishes may attract the consumers and give better flavors to them. This carotenoid pigment plays key roles in the physiological metabolism of human as well as animals, with known effects such an enhancement of immunological function, an antioxidant activity, a prevention of cancer and senescence, etc.

Because of increasing interests in *Phaffia rhodozyma* and pigments produced thereby, there have been a number of reports concerning a culture of *Phaffia rhodozyma*. However, these reports have been focused on how the inexpensive materials can be used for its culture, and have resulted in the development of method for culturing *Phaffica rhodozyma*, in which various local products may be employed, such as alfalfa juice (Okagbue et al., *Appl. Microbiol. Biotechnol.*, 20, 33, 1984), molasses (Haard et al., *Biotechnol. Lett.*, 10, 609, 1988), the byproducts of grape juice processing (Lango et al., *Biotech. Forum Europe*, 9, 565, 1992), peat hydrolyzate (Martin et al., 58, 223, 1993), the byproducts of corn wet-milling (Hayman et al., *J. Ind. Microbiol.*, 14, 389, 1995), and the mixture of sugar cane extract, urea and phosphoric acid (Fontana, et al., *Appl. Biochem. Biotechnol.*, 57/58, 413, 1996).

Although little is known about the genetics of *Phaffia rhodozyma*, the physiological features of *Phaffia rhodozyma* have been disclosed and the *Phaffia rhodozyma* mutant producing the pigment with high level has recently been selected (Johnson et al., *Crit. Rev. Biotechnol.*, 11, 297, 1991; An et al., *Appl. Environ. Microbial.*, 55, 116, 1989; Chumpolkulwong et al., *J. Ferment. Bioeng.*, 75, 375, 1997; Lewis et al., *Appl. Environ. Microbiol.*, 56, 2944, 1990). In addition, a genetic analysis enlightened the ploidy and sexual cycle of *Phaffia rhodozyma*. In a flow cytometry study, Calo-Mata and Johnson found that no strain was haploid and that most were polyploid (Calo-Mata et al., *Yeast Gen. Mol. Biol. Meet.*, 126, 1996). A pedogamic sexual process of conjugation has been also desclosed (Golubev et al., *Yeast*, 11, 101, 1995).

Although *Phaffia rhodozyma* is potentially useful for the production of astaxanthin and the like, the pigment level in the wild type of *Phaffia rhodozyma* is very low. Therefore, there have been attempts to develop a novel mutant strain of *Phaffia rhodozyma*, which can produce the pigment more than usual one. However, these attempts have been hampered by the reduced growth rate and genetic instability of said mutant, which may occur when the pigment content in the mutant exceeds over the optimal range.

Another obstacle to the progress of the mutant is the method for mutagenesis. Chemical mutagenesis procedures have been performed conventionally, but it is associated with the simultaneous mutation of undesired genes leading to pleiotropic effects such as the reduction of growth rate, the prolonged induction time in the fermentation, etc. Furthermore, because the genome of the mutant strain is not stable, its subculture often decreases the yield of the pigment.

To solve these problems in the conventional breeding procedures and to enlarge the applicability of *Phaffia rhodozyma*, molecular breeding approaches have been initiated recently, using genetic transformation. However, since most of *Phaffia rhodozyma* strains are polyploid and thus cannot be made to be an auxotrophic variant by the method conventionally applied to yeast, it is preferable to employ an approach using antibiotics-resistant genes as selectable markers. More recently, there was reported a transformation system in which *Phaffia rhodozyma* actin promoter and G418-resistant gene were used for the transformation of *Phaffia rhodozyma*, However, the system showed poor transformation efficiency (Wery et al., *Gene*, 184, 89, 1997).

On the other hand, cycloheximide, an eukaryote-specific antibiotics, is applicable to the selection of yeast transformants. The target molecule of cycloheximide is ribosome and its target site is aminoacyl-tRNA binding site (A site) of ribosome, wherein it blocks peptidyl transferase activity of ribosome. As a result, it inhibits protein synthesis and cell growth in eukaryotes, without an effect on the organelles such as chloroplasts and mitochondria. Furthermore, it has been found that cycloheximide interacts with ribosomal protein L41, and that a mutation in L41 gene confers cycloheximide-resistance on the yeast transformants. Thus, cycloheximide and related mutant form of L41 gene are widely applicable to the process for transformation of yeasts.

Recent studies support the applicability of L41 gene to selectable marker in yeasts. Takagi et al. found that amino acid substitution through the mutagenesis of *Saccharomyces cerevisiae* L41 gene conferred cycloheximide-resistance, suggesting the usefulness of L41 gene as a selectable marker (Takagi et al., *J. Bacteriol.*, 174, 254–262, 1992). Mutoh et al. proposed a biotechnological tool using *Candida maltosa* L41 gene as a selectable marker (Mutoh et al., *J. Bacteriol.*, 5383, 177, 1995). As it is well known that a substitution of $56^{th}$ amino acid residue in the L41 protein conffer cycloheximide-resistant on *Candida utilis* (Keiji Kondo et al., *J. Bacteriol.*, 7171, 177, 1995), transformation system using the substitution has been developed. Similar approaches have been introduced in *Kluyveromyces lactis* and *Schwanniomyces occidentalis* (Dehoux et al., *Eur. J. Biochem.*, 213, 841–843, 1993; Pozo et al., *Eur. J. Biochem.*, 213, 849–857, 1993). On algae *Tetrahymena*, the resistance is conferred by substitution of 40th amino acid residue, methionine to glutamine (Roberts et al., *Exp. Cell. Res.*, 312, 81, 1973).

To overcome the foregoing and other disadvantages, we, the inventors of the present invention, have noted that cycloheximide and related mutation in L41 gene may be used to develop an efficient transformation system, whereby a foreign gene is stably integrated into the genome of *Phaffia rhodozyma*, and the transformants are undoubtedly selected. To develop such system, we have constructed transforming vectors comprising the antibiotics-resistant gene and the targeting gene, which is used for the stable integration of foreign gene. We transformed *Phaffia rhodozyma* with asid vectors, according to a modified method for electrotransforming *Cryptococcus neoformans*, a member of Basidiomycetes, whereto *Phaffia rhodozyma* belongs (Kim et al., *Appl. Environ. Microbiol.*, 64, 1947, 1998).

The present invention is performed by cloning and sequencing *Phaffia rhodozyma* L41 gene; modifying the L41 gene by the mutagenesis of the region responsible to cycloheximide-resistance; constructing the vectors for transforming by inserting ribosomal DNA into the modified L41 gene; transforming *Phaffia rhodozyma* with the vector by electroporation method; and verifying the stable integration of the vector into the genome of the transformants.

SUMMARY OF THE INVENTION

It is an object of the present invention to provide a vector for transforming. *Phaffia rhodozyma* efficiently.

It is a further object of the present invention to provide a recombinant vector for transforming *Phaffia rhodozyma*, which comprises the L41 protein of *Phaffia rhodozyma*.

It is an additional object of this invention to provide a L41 gene encoding the L41 protein of *Phaffia rhodozyma*, which has an antibiotics-resistant activity.

It is another object of this invention to provide a gene encoding a mutated L41 protein which can be used as a cycloheximide-resistant gene.

It is still another object of the present invention to provide a ribosomal DNA of *Phaffia rhodozyma*, which can be used to enhance the integration efficiency of foreign DNA into *Phaffia rhodozyma* genomes.

It is another object of the present invention to provide a process for transforming *Phaffia rhodozyma* by electroporation.

Further objects and advantages of the present invention will appear hereinafter.

In accordance with the present invention, the foregoing objects and advantages are readily obtained.

The present invention provides an L41 gene encoding a ribosomal protein derived from *Phaffia rhodozyma*.

In addition, this invention provides a gene encoding mutated L41 protein wherein the amino acid at the position 56 is replaced by glutamine. Since the amino acid residue is responsible for the cycloheximide-resistance, this mutated gene in a vector is useful for a selectable marker.

The present invention also provides a ribosomal DNA derived from *Phaffia rhodozyma*.

In addition, the present invention provides a recombinant vector comprising a gene encoding a protein having a cycloheximide-resistant activity and a ribosomal DNA derived from *Phaffia rhodozyma*.

In such aspect of the present invention, also provided is a recombinant vector, pTPLR1 comprising a gene encoding the muated L41 protein of *Phaffia rhodozyma* and a portion of the *Phaffia rhodozyma* ribosomal DNA.

The present invention also provides a process of transforming *Phaffia rhodozyma* with the vector by electroporation.

In a preferred embodiment of the present invention, the vector is cleaved into a linear form. In another preferred embodiment of the present invention, the linearized vector is tintroduced into *Phaffia rhodozyma* using electrophoresis. In the more preferred embodiment of the present invention the electrophoresis is conducted with conditions as follows: electric pulse is 0.8~1.2 kV; an internal resistance is 400~800 Ω; and a capacitance is 25~50 µF.

Further features of the present invention will appear hereinafter.

BRIEF DESCRIPTION OF THE DRAWINGS

FIG. 1 is nucleotide sequence of genomic DNA containing upstream promoter region and coding region of a gene encoding L41 ribosomal protein of *Phaffia rhodozyma* (SEQ ID NO: 15) and deduced amino acid sequences by the gene (SEQ ID NO: 16), wherein,
  Open boxes: TATA and CAAT sequences;
  Underlined: the position of primers;
  Bold letters: consensus sequence in splicing region of intron;
  Open circle: amino acid residue at position 56

DETAILED DESCRIPTION OF PREFERRED EMBODIMENTS

The present invention is based upon the notion that cycloheximide and related mutation in a gene encoding L41 protein may be used to develop a transformation system, whereby a foreign gene is stably integrated into the genome of *Phaffia rhodozyma*, and the transformants are undoubtedly selected.

Hereinafter, the present invention is described in detail.

In one aspect, the present invention provides a gene encoding a L41 *Phaffia* ribosomal protein.

In a preferred embodiment, the genomic and cDNA sequences containing a gene encoding a L41 *Phaffia rhodozyma* ribosomal protein are prepared from a *Phaffia rhodozyma* strain (ATTC 24230).

The gene encoding L41 protein identified in the present invention shows high homology with other known L41 gene derived from yeasts, but contains 6 introns which have specific sequences in 5' and 3' regions of each intron. The genomic sequence represented by SEQ ID NO: 1 contains 7 exons and 6 introns and the cDNA encoding the L41 protein has a nucleotide sequence of 1,223 bp fragment represented by SEQ ID NO: 2. The deduced amino acid sequence is SEQ ID NO: 3. The proline at position 56 is responsible for sensitivity to cycloheximide (see FIG. 1).

In another preferred embodiment, the cloned gene encoding L41 protein is modified by site-directed mutagenesis, so that the mutated L41 protein has a cycloheximide-resistant activity. Particularly, a mutagenesis is performed to substitute the proline residue with glutamine, at the position 56 (see FIG. 2).

The mutagenesis in the present invention includes all the possible modification of triplet codon in the amino acid position 56. For example, the codons for proline 56 may be replaced by all possible triplet codons for glutamine.

The present invention also provides a ribosomal DNA (hereinafter "rDNA") derived from *Paffia* yeast.

In this invention, rDNA means not only a DNA sequence which is transcribed to bear all types of eukaryotic ribosomal RNA, but also a non-transcription spacer (hereinafter, "NTS"), or a DNA sequence between the transcribed rDNA. rDNA can be preferably used to enhance the integration efficiency of foreign DNA into host genomes because rDNA sequence is highly repeated as tandem units in the eukaryotic genomes.

In a preferred embodiment, the rDNA is represented by SEQ ID NO: 4. The rDNA sequence contains NTS.

The present invention provides a recombinant vector for transforming *Phaffia rhodozyma*, comprising a cycloheximide-resistant gene and a rDNA.

According to one preferred embodiment, the cycloheximide-resistant gene is a gene coding a mutated L41 protein derived *Phaffia rhodozyma*.

According to one preferred embodiment, the rDNA may be used to enhance the integration efficiency of foreign DNA into the host genome.

According to more preferred embodiment, the rDNA has a sequence of SEQ ID NO: 4.

Figure 2:
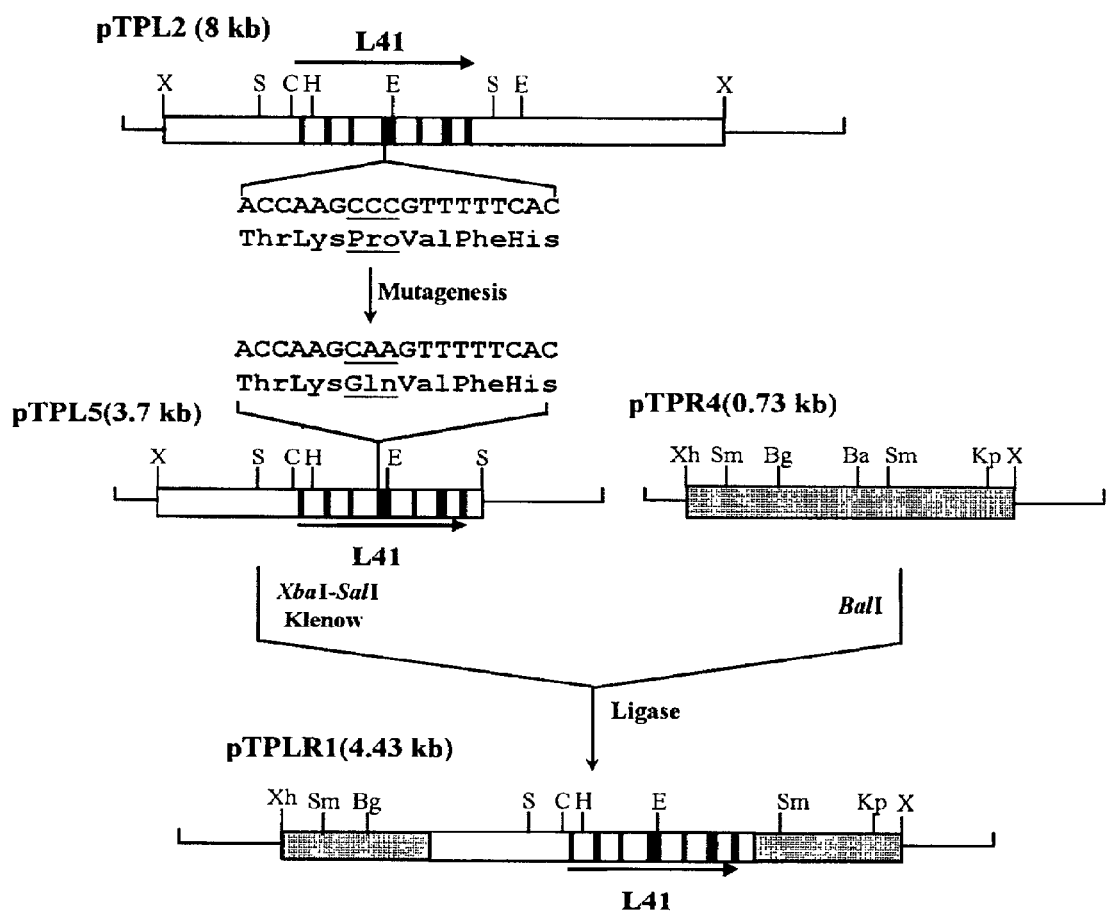
FIG. 2 represents the construction of the pTPLR1 vector, its restriction map, a nucleotide sequcence for mutagenesis of L41 gene (SEQ ID NO: 17) and its amino acid sequence (SEQ ID NO: 18) and a mutated nucleotide sequence (SEQ ID NO: 19) and its amino acid sequence SEQ ID NO:20, wherein,
  Numbers in parentheses: the sizes of inserts;
  Blank boxes: DNA fragment containing L41 gene;
  Grey boxes: rDNA fragments;
  Black boxes: exons of L41 gene;
  Thin lines: pBluescript SK(+) sequence;
  Horizontal arrow: transcriptional direction of L41 gene;
  X: XbaI site; S: SalI site; C: ClaI site;
  H: HindIII site; E: EcoRI site; Xh: XhoI site;
  Sm: SmaI site; Bg: BglI site; Ba: BalI site;
  Kp: KpnI site.

According to another preferred embodiment, the gene encoding L41 protein of *Phaffia rhodozyma* is modified so as to have a cycloheximide-resistant acitivity and be used as a selectable marker in the recombinant vector (see FIG. 2). This recombinant vector is useful for a stable transformation of a foreign gene into a host genome.

Figure 3:
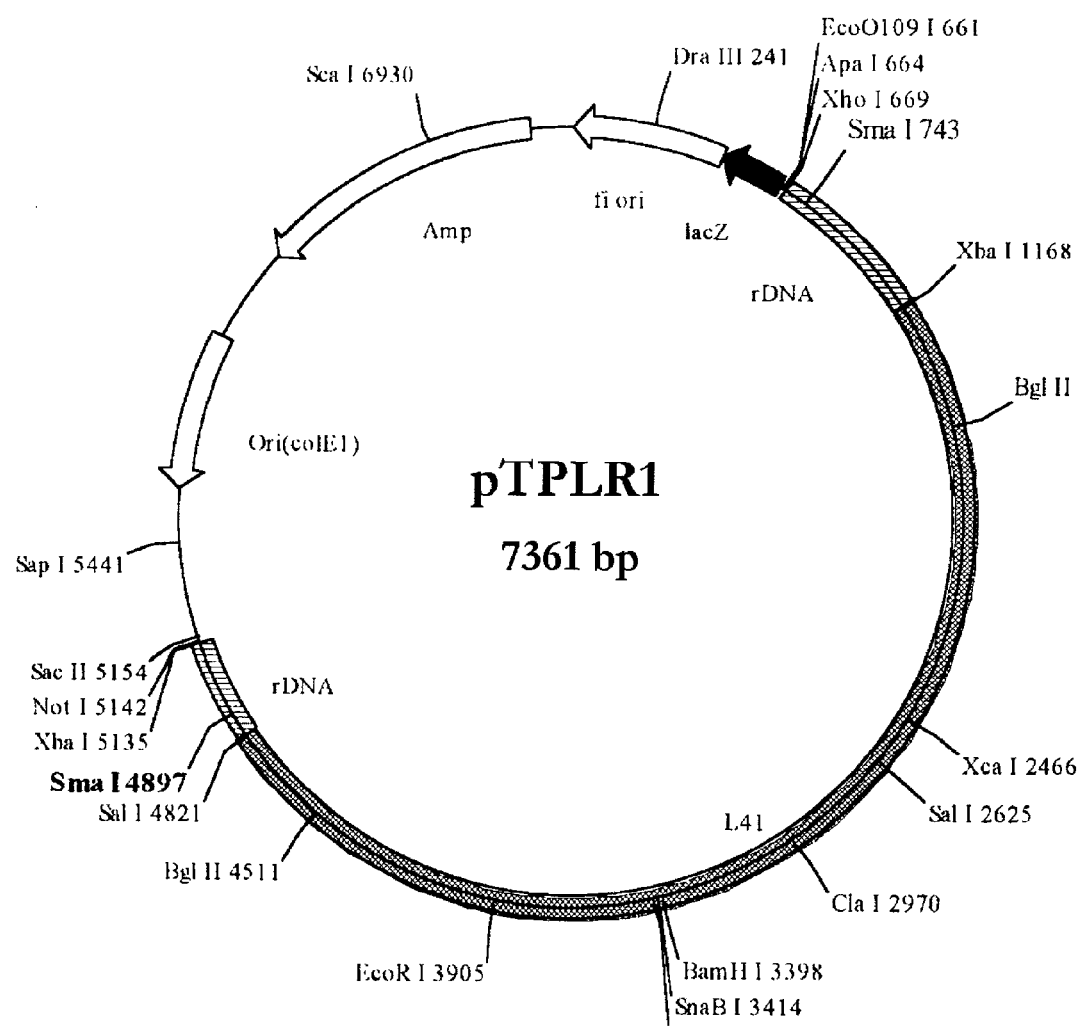
FIG. 3 represents the restriction map of pTPLR1, the vector of the present invention.

More particularly, the present invention provides pTPLR1, a vector for transforming yeasts. In the most preferred embodiment the recombinant vector comprises an NTS portion of *Phaffia rhodozyma* rDNA and a gene encoding a mutated L41 protein of *Phaffia rhodozyma* wherein the codon for proline at amino acid position 56 is substituted with the codon for glutamine (see FIG. 3).

The recombinant vector of the present invention may be readily modified and improved within the spirits and scope of the present invention. For example, the recombinant vector of the present invention may include diverse L41 genes modified using various mutagenesis procedures and diverse rDNA sequences derived from various organisms.

In another aspect of the present invention, also provided is a process for transforming yeasts with foreign DNA. The process is based upon the established method for transforming *Cryptococcus neoformans*, but optimized to yeasts, using an antibiotics-resistance gene derived from yeasts instead of the bacterium-derived counterpart.

In a preferred embodiment, the recombinant vector is cleaved into a linear form before transformation. The restriction enzymes used and the reaction may be selected carefully so that the foreign DNA is efficiently introduced into a host genome and only desired sequences of the vector are inserted to the host genome.

In the process for transforming of the present invention, an electroporation procedure is employed. According to another embodiment, electroporation is conducted with conditions as follows: an electric pulse of 0.8–1.2 kV, an internal resistance of 400–800 Ω, and a capacitance of 25–50 μF. After electroporation, the yeast cells are cultivated at 23° C. for 14–16 hours, then spread on solid medium containing cycloheximide, and further cultivated at 23° C. for 4–5 days. Assessing the effects of various conditions for the electroporation on the cell viability and the transforming efficiency (see FIG. 4) reveals that abundant transformants are produced under such condition as electric pulse of 0.8 kV, an internal resistance of 600 Ω, and a capacitance of 50 μF.

Figure 5:
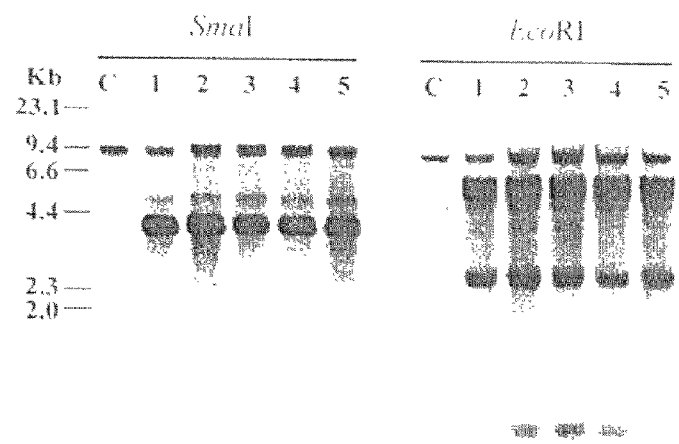
FIG. 5 represents Southern blot analysis of pTPLR1 transformants, wherein,
  C: nontransformant control;
  1 to 5: pTPLR1 transformants.
Figure 6:
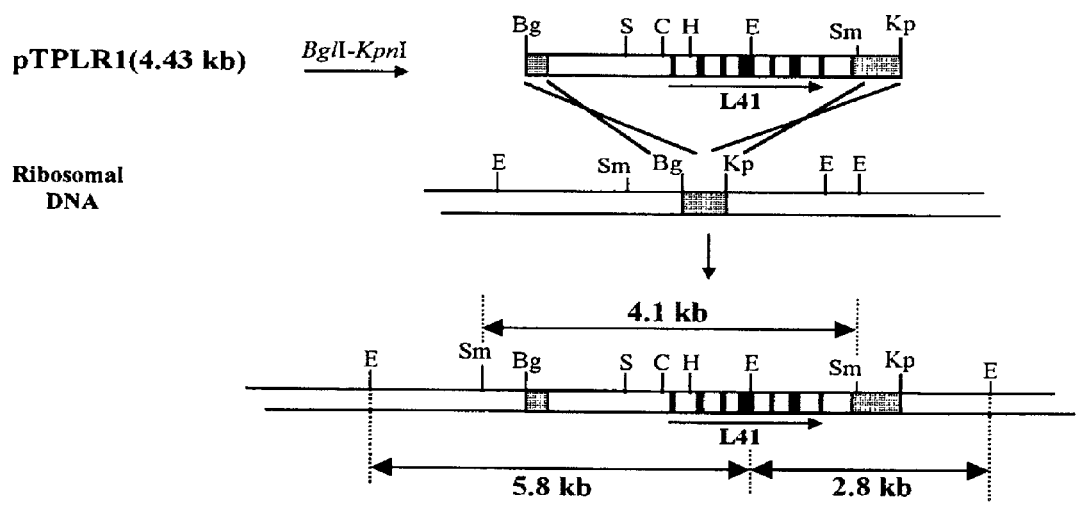
FIG. 6 is a schematic diagram showing the mode of pTPLR1 integrated into the chromosome.

In another embodiment, Southern blot analysis is used to verify the stable integration of foreign DNA (see FIGS. 5 and 6). The result confirms that the introduced genes are stably maintained in host genome, even after multiple subcultures on the medium without cycloheximide.

EXAMPLES

Practical and presently preferred embodiments of the present invention are illustrative as shown in the following Examples.

However, it will be appreciated that those skilled in the art, on consideration of this disclosure, may make modifications and improvements within the spirit and scope of the present invention.

Example 1

The Isolation of Gene Encoding a L41 Protein of *Phaffia rhodozyma*

To isolate genomic DNA sequence encoding *Phaffia rhodozyma* ribosomal protein L41, we synthesized two PCR (polymerase chain reaction) primers, the sequences thereof were deduced from the nucleotide sequence of other yeast L41 genes and represented by SEQ ID NO: 5 (CYH1) and SEQ ID NO: 6 (CYH3). PCR was performed using the synthetic oligonucleotides, CYH1 and CYH3 as PCR primers and genomic DNA isolated from *Phaffia rhodozyma* (ATCC 24230) as template. A DNA fragment of 700 bp containing a gene encoding L41 protein was produced as a result, and then was brought to a labeling reaction using digoxigenin (DIG)-labeling kit (Boehringer Mannheim, Germany) so as to be used as a probe for Southern blot analysis. To clone full-length genomic DNA encoding L41 protein, Southern blot hybridization was performed as desclosed by Sambrook et al. (Sambrook et al., *Molecular Cloning*, 2nd Edition, Cold Spring Harbor Laboratory Press, 1989) in a solution containing 5×SSC, 0.1% (w/v) sarcosyl, 0.02% (w/v) SDS, 5% blocking agent, and 50% (v/v) formamide, at 42° C. A strong hybridization signal was observed from an 8-kb XbaI fragment, and the XbaI fragments of 7 to 9-kb were isolated and ligated into pBluescript SK(+) (Stratagene, USA) to make a minilibrary. A clone (pTPL2), hybridizing with the PCR product was identified in a further Southern blot analysis wherein the DNA fragment of the minilibrary were blotted onto the membrane.

To identify the gene encoding L41 protein without intron, *Phaffia rhodozyma* L41 cDNA was isolated by the method of rapid amplification of cDNA ends (RACE) with 3'-RACE (GIBCO BRL, USA) and 5'-RACE (Clontech, USA) kits. Total RNA was prepared by the method of Elion and Warner (Elion et al., *Cell,* 39, 663–673, 1984). Then mRNA was selected from the total RNA, using mRNA isolation kit (Novagen), and a 3' RACE reaction was performed with a synthetic oligonucleotide represented by SEQ ID NO; 7 as a 3' RACE primer, and 5' RACE reaction was ferformed with a synthetic oligonucleotide represented by SEQ ID NO: 8 as a 5' RACE primer.

The sequencing of the 3' and 5' RACE products suggested that a putative open reading frame of 1,223 bp be interrupted by six introns. The cloned gene encoding L41 protein was found to show high homology with those of other yeasts. However, the number of introns and their organization in the gene encoding the L41 protein of *Phaffia rhodozyma* were quite different from those of the other yeast. In fact, they have only one intron. GTPuNGT sequence and PyAG sequence were conserved in 5' and 31 ends, respectively, of the gene encoding L41 protein of *Phaffia rhodozyma*; this conserved sequences were also reported in the intron of actin of *Phaffia rhodozyma.* The L41 gene encodes ribosomal protein comprising 106 amino acids, and most notably, proline at position 56 is identified to the amino acid residue responsible for the sensitivity to cycloheximide. The genomic DNA sequence of the gene encoding L41 protein of *Phaffia rhodozyma* was registered in GenBank on May 19, 1997, with accession NO. AF 004672 (see FIG. 1 and SEQ ID NO: 15).

Example 2

A Gene Encoding Mutant L41 Protein having Cycloheximide-Resistant Activity

To confer the cycloheximide-resistance on the genen encoding the L41 protein, we performed a site-directed mutagenesis which resulted in the amino acid substitution proline at position 56 with glutamine. Particularly, mutagenesis was carried out with the QuickChange in vitro mutagenesis kit (Stratagene) as described in the manufacturer's instructions with complementary mutagenic primers corresponding to amino acids 52 to 59 represented by SEQ ID NO: 9 and 10. The 2.2-kb SalI fragment digested from the 8.0-kb fragment in Example 1 was replaced with the mutated fragment.

Example 3

The Isolation of Ribosomal DNA

Ribosomal DNA (rDNA) in the present invention was exploited to enhance the integration efficiency of foreign DNA into *Phaffia rhodozyma* genomes. To clone the rDNA fragment, two pairs of PCR primers, represented by SEQ ID NO: 11, 12 (corresponding to 18 S rDNA part) and 13, 14 (corresponding to 28 S rDNA part), were designed from the known partial rDNA sequence of *Phaffia rhodozyma.*

By PCR with these two pairs of primers, two DNA fragments were obtained. One of those was 1.5-kb fragment containing the 5.8 S rDNA NTS (non-transcription spacer) region with the primers represented by SEQ ID NO: 11 and 14, and the other was 6-kb fragment containing the 5 S rDNA NTS region with the primers represented by SEQ ID NO: 12 and 13.

Two DNA fragments were used as a probe for cloning the rDNA unit in genomic Southern blot analysis, followed by the construction of minilibrary, as described in Example 1. Multiple rounds of Southern blot hybridization identified an 8.5-kb HindIII fragment, which was cloned and identity thereof was confirmed by partial sequencing. A 730-bp XhoI and XbaI fragment of the 8.5-kb fragment, which spans NTS region between 5 S and 18 S rDNA, was subcloned in pBluescript and the resulting vector was designated as pTPR4. A sequencing of pTPR4 enlightened that the cloned rDNA fragment showed high homology with 5.8 S and 25 S rDNA region of *Candida neoformans,* a member of Basidiomycetous yeasts including *Phaffia rhodozyma.* The 730-bp nucleotide sequence of *Phaffia rhodozyma* rDNA gene was registered in GenBank on Jul. 28, 1997, with accession NO. AF 016256.

Example 4

The Construction of Recombinant Vector for Transforming *Phaffia rhodozyma*

To construct recombinant vectors for transforming *Phaffia rhodozyma* efficiently, we constructed pTPL5 vector containing the gene encoding mutated L41 protein prepared in Example 2 and pTPR4 vector containing the rDNA fragment prepared in Example 3 (see FIG. 2). Particularly, pTPLR1 which is a recombinant vector for transforming *Phaffia rhodozyma* was cunstructed using the 3.7-kb fragment of pTPL5 as a cycloheximide-resistant marker and the 730-bp rDNA fragment of pTPR4 as a targeting sequence whereby a forein DNA is integrated into *Phaffia rhodozyma* genome with multicopy. The 3.7-kb XbaI-SalI fragment of pTPL5 containing the gene encoding a mutated L41 protein was treated with the Klenow enzyme and inserted into the BalI site of pTPR4. The resulting plasmid, pTPLR1 (see FIG. 3), was introduced into *E. coli* DH5α strain, and the transformed *E. coli* strain was deposited in Korean Collection for Type Cultures (KCTC) on Oct. 21, 1998 (accession NO: KCTC 0535BP).

We also constructed a plasmid, pTPLR2, which has the reverse direction agaist the coding sequences. The pTPLR1 and pTPLR2 vectors were digested with SmaI or BglI-KpnI restriction enzymes, before the vector was brought to the transformation and integrated into the rDNA region of *Phaffia rhodozyma* genome.

Example 5

The Transformation of *Phaffia rhodozyma* with pTPLR1 Vector

To transform *Phaffia rhodozyma* with the pTPLR1 vector efficiently, we developed the transformation method, which is based upon the method for transforming a Basidiomycetous yeast, *Cryptococcus neoformans* (Varma et al., *Infect. Immun.,* 60, 1101, 1992) but optimized for *Phaffia rhodozyma*. Electroporation procedure was employed in the process of the present invention. Particularly, *Phaffia rhodozyma* cells from a log-phase cluture in 50 ml of YM medium were harvested by centrifuge at 3,000 rpm for 10 minutes, then washed twice with equal volume of electroporation buffer (270 mM sucrose, 10 mM Tris, 1 mM $MgCl_2$, pH 8.0) containing 1 mM dithiothreitol (DTT), and resuspended in the electroporation buffer without DTT. The linearized plasmid pTPLR1 (200 ng) was mixed with a 50 μl aliquot (approximately $2 \times 10^7$ cells) of the cell suspension, and transferred to a cuvette (0.2-cm electrode gap; Bio-Rad, USA). Sets of electroporation were performed (Gene Pulser II; Bio-Rad, USA) under the various ranges of electric pulse (0.8 to 1.2 kV), internal resistance (400 to 800 Ω) and capacitance (25 to 50 μF). The electroporated cells were resuspended in 1 ml of YM medium and transferred to a test tube for incubation. After being shaken for 12 to 16 hours at 23° C., cells were spread on YM agar medium containing 10 μg/ml of cycloheximide and incubated at 23° C. for 4 to 5 days.

Figure 4:
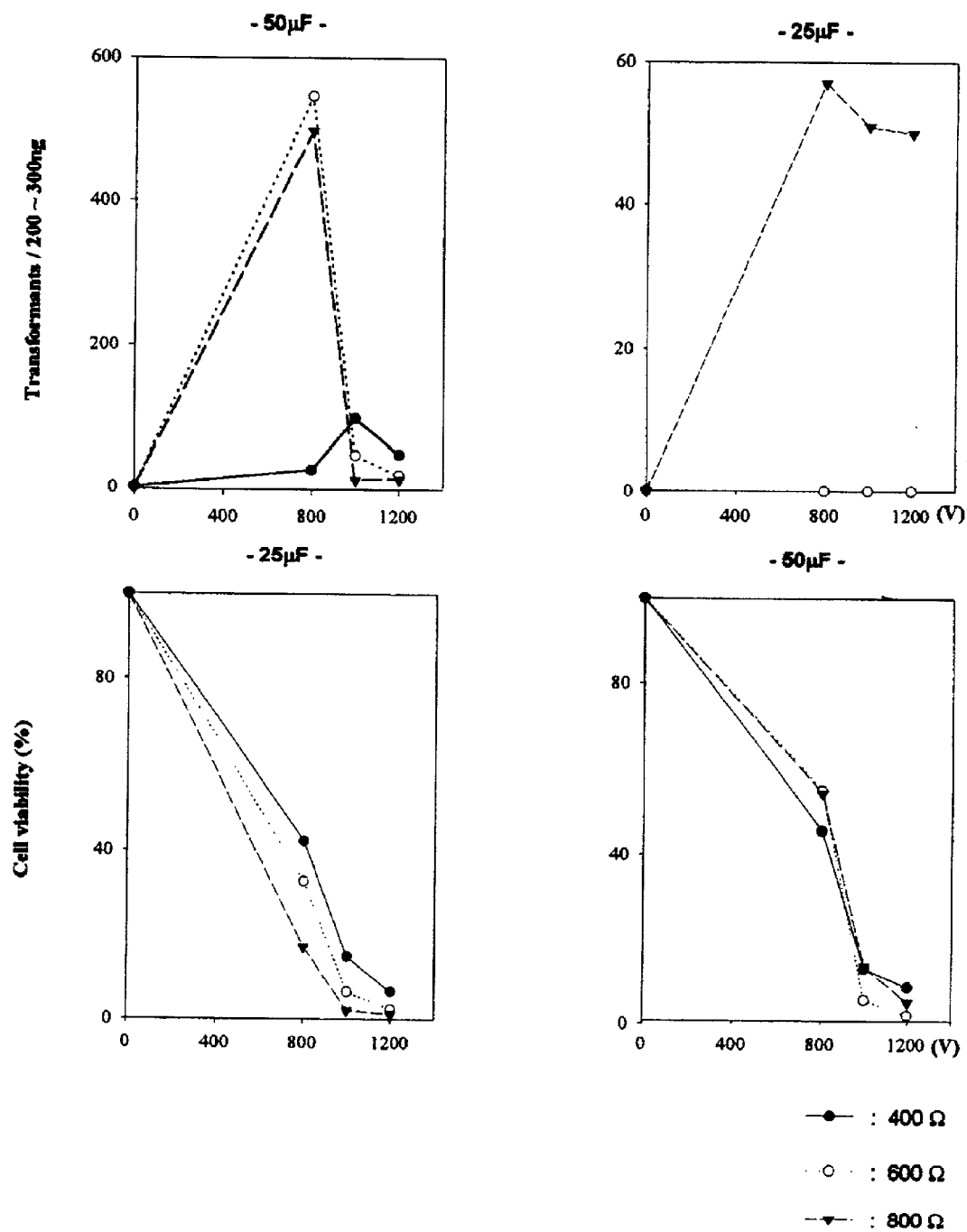
FIG. 4 represents the relationship between the condition of electroporation and the transformation efficiency or cell viability.

FIG. 4 shows the relationship between the condition of electroporation and the transformation efficiency or cell viability. The transformation efficiency was mainly dependent on the capacitance, preferably of 50 μF rather than 25 μF. In summary, more transformants were produced when an electric pulse of 0.8 kV was delivered and internal resistance of 600 Ω was set with a capacitance of 50 μF, generating pulse lengths of 18 to 20 Ms. Under such a condition, approximately 30% of cells survived, and transformation efficiencies of 800 to 1000 transformants per μg of DNA could be routinely obtained with pTPLR1 linearized either by SmaI or by BglI-KpnI.

Using the optimized process, we transformed *Phaffia rhodozyma* with various vectors and observed the colony formation on the YM agar medium containing cycloheximide.

Interestingly, there was no transformant with pTPLR2 in any condition, suggesting that L41 gene is expressed only when the transcriptional direction of the integrated L41 gene is the same as that of rDNA.

Without the linearization of pTPLR1 before transformation, no colony was formed. This may result from the fact that rDNA does not have the autonomous replication sequence (ARS) or its similar function.

A vector carrying a gene encoding a mutated L41 protein having cycloheximide-resistant activity but not containing rDNA sequence, was introduced into *Phaffia rhodozyma*. In this case, a few colonies were observed. We suspected that the mutated L41 gene in the vector would replace endogenous L41 gene in the genome, rather than be integrated in directed position.

In addition, we transformed *Phaffia rhodozyma* with a vector wherein the promoter of L41 gene was deleted, and observed transformed colonies. The Southern blot analysis of this transformant showed the same hybridization pattern as that of nontransformant control. This indicates that the a substitution has occurred in this case, rather than an integration in the directed position.

Example 7

Southern Blot Analysis of the Transformants

To assess the stability of the introduced foreign DNA in *Phaffia rhodozyma* genome according to the present invention, a Southern blot analysis of genomic DNA, which is prepared from pTPLR1 transformants or nontransformant control was performed (see FIG. 5). Particularly the genomic DNA was digested with SmaI or EcoRI enzyme, and the 2.2-kb SalI fragment of pTPL2 was used as a probe in the hybridization. The intensity of colored band was measured by the scanning densitometer (Model GS-700 Imaging Densitometer, Bio-Rad, USA).

Southern blot analysis, wherein genomic DNA of transformants was digested with SmaI, showed two colored bands at 9.0-kb and 4.1-kb. A signal at 9.0-kb is observed both in a nontransformant control and in the transformants, indicating that this band originated form the endogenous gene encoding L41 protein of Phaffia rhodozyma. A much stronger signal at 4.1-kb also was detected in transformants, but not in the control. This was identical with the result of the restriction map of the transforming plasmid (see FIG. 6). The size and relative intensity of signal at 4.1-kb suggested that multiple copies (approximately, 7 copies) of the transforming plasmid had been integrated.

In another Southern blot analysis with EcoRI digestion, two bands at 5.8-kb and 2.8-kb were found only in transformants (see FIG. 5). The 5.8-kb band originated from a 3.2-kb rDNA fragment and a 2.6-kb L41 gene fragment, and the 2.8-kb band originated from a 1.7-kb rDNA fragment and a 1.1-kb L41 gene fragment. Integration may occur as diagrammed in FIG. 6.

These results were reproducible in Southern blot analysis with rDNA probe. Most importantly, copy number did not decrease after a prolonged cultivation in YM medium with or without cycloheximide, indicating that the transforming plasmid was integrated into the chromosome and maintained stably.

INDUSTRIAL APPLICABILITY

As shown above, the vector for transforming *Phaffia rhodozyma* of the present invention comprises rDNA and a gene encoding a mutated L41 protein having cycloheximide-resistant activity, which is useful for a stable integration of foreign DNA into host genome and for a convenient selection of transformants, respectively. The vector of the present invention is, therefore, applicable to the transformation of yeast cells including *Phaffia rhodozyma*, in combination with the process for transforming yeast cells of the present invention, wherein the yeast cells are transformed through the optimized electroporation.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

What is claimed is:

1. An isolated ribosomal DNA of *Phaffia rhodozyma* having the nucleotide sequence of SEQ ID NO: 4.

2. A recombinant vector comprising a cycloheximide-resistant gene and a *Phaffia rhodozyma* ribosomal DNA, wherein the nucleotide sequence of the *Phaffia rhodozyma* ribosomal DNA is SEQ ID NO: 4.

3. A process for transforming yeast, said process comprising transforming said yeast with the vector of claim 2.

4. The process according to claim 3, wherein the yeast is *Phaffia rhodozyma*.

5. The process according to claim 3, wherein the vector is cleaved into a linear form.

6. The process according to claim 3, wherein the transformation is performed by electroporation under an electric pulse of 0.8~1.2 kV, an internal resistance of 400~800 Ω, and a capacitance of 25~50 µF.

* * * * *

UNITED STATES PATENT AND TRADEMARK OFFICE
CERTIFICATE OF CORRECTION

PATENT NO.        : 6,987,026 B1
APPLICATION NO. : 09/830691
DATED             : January 17, 2006
INVENTOR(S)       : Choi et al.

It is certified that error appears in the above-identified patent and that said Letters Patent is hereby corrected as shown below:

Title page,

Item [73], Assignees:
Lines 2 and 3, please delete "Haitai Confectionery Co., Ltd., Seoul (KR)".

Signed and Sealed this

Fourth Day of December, 2007

JON W. DUDAS
*Director of the United States Patent and Trademark Office*

SEQUENCE LISTING

<160> NUMBER OF SEQ ID NOS: 20

<210> SEQ ID NO 1
<211> LENGTH: 1223
<212> TYPE: DNA
<213> ORGANISM: Phaffia rhodozyma

<400> SEQUENCE: 1

-continued

```
atggtcaacg ttcccaagac tcgacgtgag ttatagcaat ttcaacaact ctccagacga      60
caaatattcc agtgcatcga aagagtttgt ggataaacgc gacagtttca agggaaagag     120
tcgatggaca gatttggaag acttagccgg tcaaggaact tggggatcac gtggcggagg     180
actcatcaga agaagtcggg atttgtttga tcatagtggg atcaagacaa actggaggat     240
atggctcgcc ttggaaggga atctccggcc tggattcgag gatccgaaag ttgtacgtat     300
ggaaaagctt acacggcttg gatttattat ctttcatagg aacctactgc aagggtaagg     360
cttgcaagaa gcacacgtaa gtcgcttatc ctctccactc tttcatggca tattgtcaac     420
gactggacaa cgcgtccgtt ttgaaacaag tgacttacct gtgaaatttg attctacacc     480
tgtatttagc cctcacaagg tacatatcac atcctcccac cccaccctgc ccaacttctt     540
cagttcatct tgctctcggt ttccacattc cctgatgacc tccttgtatg ttctttgcga     600
acgtttgttt ctgtttctgt aggtgaccca gtacaagaag ggaaaggact ccatcttcgc     660
ccagggaaag cgacgatacg accgaaagca gtccggttac ggaggtcaga ccaagcccgt     720
tttccacaag aaggctaaga ccaccaagaa ggtcgtcctt cgattggcgg tattttttgtt    780 tattttgaat tcttttttgtg tatgcagact tttgatgatt atgctcctct gtcgtttttt    840
ctcttcaaac agagtgctcc gtctgcagtt cgttcttcct tccaaccaaa acttcaacta     900
cagacatcat aaacagacat cttacttcgg tgttctctct ttttttccgc agagtacaag     960
atgcagatga ccctcaagcg atgcaagcac ttcgagcttg gaggagacaa gaagaccaag    1020
ggttcgtctt ttgtccatat attctctggt tcacttctta tgttcctaac gtacttgttt    1080
cctttttggt tcggatgttg tttctatcgg tggtgttttc ttttctttgg atgcattatc    1140
atttatcgtg ttggactgtt ttcctctgct cgtttctttc cctctgtac ttgtgcttct     1200 caggagccgc catctctttc taa                                             1223
```

```
<210> SEQ ID NO 2
<211> LENGTH: 350
<212> TYPE: DNA
<213> ORGANISM: Phaffia rhodozyma
<220> FEATURE:
<221> NAME/KEY: CDS
<222> LOCATION: (30)...(347)

<400> SEQUENCE: 2
```

```
cccttcaagt ctcgtctcaa tcagtcaag atg gtc aac gtt ccc aag act cga       53
                                Met Val Asn Val Pro Lys Thr Arg
                                  1               5 cga acc tac tgc aag ggt aag gct tgc aag aag cac acc cct cac aag      101
Arg Thr Tyr Cys Lys Gly Lys Ala Cys Lys Lys His Thr Pro His Lys
         10                  15                  20 gtg acc cag tac aag aag gga aag gac tcc atc ttc gcc cag gga aag      149
Val Thr Gln Tyr Lys Lys Gly Lys Asp Ser Ile Phe Ala Gln Gly Lys
 25                  30                  35                  40 cga cga tac gac cga aag cag tcc ggt tac gga ggt cag acc aag ccc      197
Arg Arg Tyr Asp Arg Lys Gln Ser Gly Tyr Gly Gly Gln Thr Lys Pro
                 45                  50                  55 gtt ttc cac aag aag gct aag acc acc aag aag gtc gtc ctt cga ttg      245
Val Phe His Lys Lys Ala Lys Thr Thr Lys Lys Val Val Leu Arg Leu
             60                  65                  70 gag tgc tcc gtc tgc aag tac aag atg cag atg acc ctc aag cga tgc      293
Glu Cys Ser Val Cys Lys Tyr Lys Met Gln Met Thr Leu Lys Arg Cys
         75                  80                  85 aag cac ttc gag ctt gga gga gac aag aag acc aag gga gcc gcc atc      341
```

```
Lys His Phe Glu Leu Gly Gly Asp Lys Thr Lys Gly Ala Ala Ile
         90                  95                 100 tct ttc taa                                                              350
Ser Phe
105

<210> SEQ ID NO 3
<211> LENGTH: 106
<212> TYPE: PRT
<213> ORGANISM: Phaffia rhodozyma

<400> SEQUENCE: 3

Met Val Asn Val Pro Lys Thr Arg Arg Thr Tyr Cys Lys Gly Lys Ala
 1               5                  10                  15

Cys Lys Lys His Thr Pro His Lys Val Thr Gln Tyr Lys Lys Gly Lys
            20                  25                  30

Asp Ser Ile Phe Ala Gln Gly Lys Arg Arg Tyr Asp Arg Lys Gln Ser
        35                  40                  45

Gly Tyr Gly Gly Gln Thr Lys Pro Val Phe His Lys Lys Ala Lys Thr
    50                  55                  60

Thr Lys Lys Val Val Leu Arg Leu Glu Cys Ser Val Cys Lys Tyr Lys
65                  70                  75                  80

Met Gln Met Thr Leu Lys Arg Cys Lys His Phe Glu Leu Gly Gly Asp
                85                  90                  95

Lys Lys Thr Lys Gly Ala Ala Ile Ser Phe
             100                 105

<210> SEQ ID NO 4
<211> LENGTH: 741
<212> TYPE: DNA
<213> ORGANISM: Phaffia rhodozyma
<220> FEATURE:
<221> NAME/KEY: misc_feature
<222> LOCATION: (0)...(0)
<223> OTHER INFORMATION: n=a, t, c, or g

<400> SEQUENCE: 4
ctcgagtgga cggtggcaat ggcattcgtg tcgttggtgc tcactcgcaa cccaagcagt      60
cgcttacccg gggtagcctc cgggtgggcg cgatgatttg tggtgtggat tccttccccta    120 tgggtagaac gacgcgcaac caatcattcg gagaaccgct ccgttgtagc cgaccagtct    180
gattgatcaa catgccagca cgtcctccgg gacggagact ggcggggatc gtacctcatc    240
tggaatcgct ggctcaatgg tagtagtctt cacgatcggc catgagggca gtctaggtgg    300
gttcgcctgc cgaagactgt gtgagtgtgc tganaactaa ttgagtaccg ggggataagg    360
caaggcgtgt ntggttgccg gtggctgtga gcgagtttgc tgcaaagcga ttcaatgcac    420
cccggcttgg ccagcgcgct gcgtcacgaa acacactaaa cggttgacgc cataaagtaa    480
taacacactc aagtttgtgg tcccgggtgg gcctctgtgc ctgcgtggga cccgacggga    540
gaggaaaacg ttctgtggcc ctctcctctg tggatagtta cctggttgat cctgccagta    600
gtcatatgct tgtctcaaag attaagccat gcatgtctaa gtataaacaa attcatactg    660
tgaaactgcg aatggctcat taaatcagtt atagtttatt tgatggtacc ttgctacatg    720
gataactgtg gtaattctag a                                              741

<210> SEQ ID NO 5
<211> LENGTH: 23
<212> TYPE: DNA
<213> ORGANISM: Artificial Sequence
```

```
<220> FEATURE:
<223> OTHER INFORMATION: CYH1, a PCR primer for the cloning of L41
      genomic DNA fragment
<220> FEATURE:
<221> NAME/KEY: misc_feature
<222> LOCATION: (0)...(0)
<223> OTHER INFORMATION: n=a, t, c, or g

<400> SEQUENCE: 5
cgcgtagtta aygtnccnaa rac                                         23

<210> SEQ ID NO 6
<211> LENGTH: 25
<212> TYPE: DNA
<213> ORGANISM: Artificial Sequence
<220> FEATURE:
<223> OTHER INFORMATION: CYH3, a PCR primer for the cloning of L41
      genomic DNA fragment

<400> SEQUENCE: 6
cccgggtytt ggcyttyttr tgraa                                       25

<210> SEQ ID NO 7
<211> LENGTH: 24
<212> TYPE: DNA
<213> ORGANISM: Artificial Sequence
<220> FEATURE:
<223> OTHER INFORMATION: 3' RACE primer

<400> SEQUENCE: 7
ggtcagacca agcaagtttt tcac                                        24

<210> SEQ ID NO 8
<211> LENGTH: 24
<212> TYPE: DNA
<213> ORGANISM: Artificial Sequence
<220> FEATURE:
<223> OTHER INFORMATION: 5' RACE primer

<400> SEQUENCE: 8
gtgaaaaact tgcttggtct gacc                                        24

<210> SEQ ID NO 9
<211> LENGTH: 24
<212> TYPE: DNA
<213> ORGANISM: Artificial Sequence
<220> FEATURE:
<223> OTHER INFORMATION: sense primer for the mutagenesis of L41 gene

<400> SEQUENCE: 9
ggtcagacca agcaagtttt tcac                                        24

<210> SEQ ID NO 10
<211> LENGTH: 24
<212> TYPE: DNA
<213> ORGANISM: Artificial Sequence
<220> FEATURE:
<223> OTHER INFORMATION: antisense primer for the mutagenesis of L41
      gene

<400> SEQUENCE: 10
gtgaaaaact tgcttggtct gacc                                        24

<210> SEQ ID NO 11
<211> LENGTH: 20
<212> TYPE: DNA
<213> ORGANISM: Artificial Sequence
```

-continued

```
<220> FEATURE:
<223> OTHER INFORMATION: a PCR primer corresponding to 18S rDNA

<400> SEQUENCE: 11
tcctagtaag cgcaagtcat                                              20

<210> SEQ ID NO 12
<211> LENGTH: 20
<212> TYPE: DNA
<213> ORGANISM: Artificial Sequence
<220> FEATURE:
<223> OTHER INFORMATION: a PCR primer corresponding to 18S rDNA

<400> SEQUENCE: 12
ttcggccaag gaaagaaact                                              20

<210> SEQ ID NO 13
<211> LENGTH: 20
<212> TYPE: DNA
<213> ORGANISM: Artificial Sequence
<220> FEATURE:
<223> OTHER INFORMATION: a PCR primer corresponding to 28S rDNA

<400> SEQUENCE: 13
aatcggatta tccggagcta                                              20

<210> SEQ ID NO 14
<211> LENGTH: 20
<212> TYPE: DNA
<213> ORGANISM: Artificial Sequence
<220> FEATURE:
<223> OTHER INFORMATION: a PCR primer corresponding to 28S rDNA

<400> SEQUENCE: 14
gctataacac atccggagat                                              20

<210> SEQ ID NO 15
<211> LENGTH: 2192
<212> TYPE: DNA
<213> ORGANISM: Phaffia rhodozyma

<400> SEQUENCE: 15
aagagctatt tgaatgacga ccacaagagt gacgatcata ttgagcatag tataccaaag      60
gccaagaggc tgtgtggtgt tctatgagtg gccttgatta tgtgttacat aaataaactg     120
atctcaattt ttcaaatact tgccaacact tcatatatt cacaccaaaa aaagtcagat      180
tggcccacaa agtcagatac acgctcgatc gtcgacgggt tcaagcactt tgtcaggcga     240
aagaaaggcc acagcaccac ccttcaagtc tcgtctcaat caggttcgtc tagcttttttg    300 tgtgcaagga tttaccgtct tgatggattt gttcgttgaa agagaggaaa gaacatgctg     360
aactgacgaa agtgtgaaca aaaaattgtg atttttttcat tgtgtttcgc tggtctcctt    420
gctgggttgg gttggatcgg atttatcttc tgtgttggat ggaaaaccct gaatgttctt     480
ttcttggaca tcttctaaac tcgacaaaac gattcattcc tccgtactgc tctggttctg    540
cctttttgaa tcgcatcgat aaattcttcc ctcggaacgt tcgatcaatc tccgtcaaac    600
ttatcatcca aaaatctctt ctcgactgcc gccttgctcc tttcttcgt tctttccttaa   660 atccgctttc gactaccctc cttctcttca cactcatagt caagatggtc aacgttccca     720
agactcgacg tgagttatag caatttcaac aactctccag acgacaaaata ttccagtgca    780 tcgaaagagt ttgtggataa acgcgacagt ttcaagggaa agagtcgatg gacagatttg     840
```

```
gaagacttag ccggtcaagg aacttgggga tcacgtggcg gaggactcat cagaagaagt     900
cgggatttgt ttgatcatag tgggatcaag acaaactgga ggatatggct cgccttggaa     960
gggaatctcc ggcctggatt cgaggatccg aaagttgtac gtatggaaaa gcttacacgg    1020
cttggattta ttatctttca taggaaccta ctgcaagggt aaggcttgca agaagcacac    1080
gtaagtcgct tatcctctcc actctttcat ggcatattgt caacgactgg acaacgcgtc    1140
cgttttgaaa caagtgactt acctgtgaaa tttgattcta cacctgtatt tagccctcac    1200
aaggtacata tcacatcctc ccaccccacc ctgcccaact tcttcagttc atcttgctct    1260
cggtttccac attccctgat gacctccttg tatgttcttt gcaacgtttt gtttctgttt    1320
ctgtaggtga cccagtacaa gaagggaaag gactccatct tcgcccaggg aaagcgacga    1380
tacgaccgaa agcagtccgg ttacggaggt cagaccaagc ccgttttttca caagaaggct    1440
aagaccacca agaaggtcgt ccttcgattg ggtacgtttt tgtttatttt gaattctttt    1500
tgtgtatgca gacttttgat gattatgctc ctctgtcgtt ttttctcttc aaacagagtg    1560
ctccgtctgc agttcgttct tccttccaac caaaacttca actacagaca tcataaacag    1620
acatcttact tcggtgttct ctcttttttt ccgcagagta caagatgcag atgaccctca    1680
agcgatgcaa gcacttcgag cttggaggag acaagaagac caagggttcg tcttttgtcc    1740
atatattctc tggttcactt cttatgttcc taacgtactt gtttccttt  tggttcggat    1800
gttgtttcta tcggtggtgt tttcttttct ttggatgcat tatcatttat cgtgttggac    1860
tgttttcctc tgctcgtttc tttctcctct gtacttgtgc ttctcaggag ccgccatctc    1920
tttctaaatg gttgttttaa ccccgtcgtc tccaccatat gtcaaatcgg catgcgcgtt    1980
gtccctttcca atcagtcgtt tccatgctcg agatacttct tggacgttct tggggagcaa    2040
ttacacatcg agaaaatacc caaaaaacca cgcaccccct tttatttcaa tggggagatc    2100
tggatctatg tatcatgtcg attttctatt tcccaaaacc cattgattgt tcatctcctc    2160
ttaagagtaa catcttttcc aagatacttc tc                                  2192
```

<210> SEQ ID NO 16
<211> LENGTH: 106
<212> TYPE: PRT
<213> ORGANISM: Phaffia rhodozyma

<400> SEQUENCE: 16

```
Met Val Asn Val Pro Lys Thr Arg Arg Thr Tyr Cys Lys Gly Lys Ala
 1               5                  10                  15
Cys Lys Lys His Thr Pro His Lys Val Thr Gln Tyr Lys Lys Gly Lys
                20                  25                  30
Asp Ser Ile Phe Ala Gln Gly Lys Arg Arg Tyr Asp Arg Lys Gln Ser
            35                  40                  45
Gly Tyr Gly Gly Gln Thr Lys Pro Val Phe His Lys Ala Lys Thr
        50                  55                  60
Thr Lys Lys Val Val Leu Arg Leu Glu Cys Ser Val Cys Lys Tyr Lys
 65                  70                  75                  80
Met Gln Met Thr Leu Lys Arg Cys Lys His Phe Glu Leu Gly Gly Asp
                85                  90                  95
Lys Lys Thr Lys Gly Ala Ala Ile Ser Phe
            100                 105
```

<210> SEQ ID NO 17
<211> LENGTH: 18
<212> TYPE: DNA

```
<213> ORGANISM: Phaffia rhodozyma

<400> SEQUENCE: 17
accaagcccg tttttcac                                                18

<210> SEQ ID NO 18
<211> LENGTH: 6
<212> TYPE: PRT
<213> ORGANISM: Phaffia rhodozyma

<400> SEQUENCE: 18

Thr Lys Pro Val Phe His
1               5

<210> SEQ ID NO 19
<211> LENGTH: 18
<212> TYPE: DNA
<213> ORGANISM: Artificial Sequence
<220> FEATURE:
<223> OTHER INFORMATION: mutation

<400> SEQUENCE: 19
accaagcaag tttttcac                                                18

<210> SEQ ID NO 20
<211> LENGTH: 6
<212> TYPE: PRT
<213> ORGANISM: Artificial Sequence
<220> FEATURE:
<223> OTHER INFORMATION: mutation

<400> SEQUENCE: 20

Thr Lys Gln Val Phe His
1               5
```